United States Patent
McVaney

(10) Patent No.: US 12,042,308 B2
(45) Date of Patent: Jul. 23, 2024

(54) SYSTEMS AND METHODS FOR SECURING MEDICAL DEVICES

(71) Applicant: Contech Medical, Inc., Providence, RI (US)

(72) Inventor: Jesse Thomas McVaney, Wakefield, RI (US)

(73) Assignee: Contech Medical, Inc., Providence, RI (US)

( * ) Notice: Subject to any disclaimer, the term of this patent is extended or adjusted under 35 U.S.C. 154(b) by 94 days.

(21) Appl. No.: 17/639,278

(22) PCT Filed: Sep. 10, 2020

(86) PCT No.: PCT/US2020/050250
§ 371 (c)(1),
(2) Date: Feb. 28, 2022

(87) PCT Pub. No.: WO2021/050768
PCT Pub. Date: Mar. 18, 2021

(65) Prior Publication Data
US 2022/0331041 A1    Oct. 20, 2022

Related U.S. Application Data

(60) Provisional application No. 62/898,840, filed on Sep. 11, 2019.

(51) Int. Cl.
*A61B 50/20*    (2016.01)
*A47F 7/00*    (2006.01)
(Continued)

(52) U.S. Cl.
CPC .............. *A61B 50/20* (2016.02); *A47F 7/005* (2013.01); *A61B 50/22* (2016.02); *F16L 3/223* (2013.01)

(58) Field of Classification Search
CPC ......... A61B 50/20; A61B 50/24; F16L 3/223; A47B 81/00; A47B 81/005; A47F 7/005; A47F 7/0028
See application file for complete search history.

(56) References Cited

U.S. PATENT DOCUMENTS 3,576,304 A * 4/1971 Gillemot ............... F16L 3/1226
24/339
3,696,920 A * 10/1972 Lahay .................... A61B 50/30
206/370

(Continued)

FOREIGN PATENT DOCUMENTS

CH        425369 A  * 11/1966
DE    29620300 U1  *  1/1997 .............. F16L 3/223
(Continued)

OTHER PUBLICATIONS

International Search Report and Written Opinion in corresponding International Application No. PCT/US2020/050250, mailed Nov. 23, 2020 (10 pages).

(Continued)

*Primary Examiner* — Stanton L Krycinski
(74) *Attorney, Agent, or Firm* — NIXON PEABODY LLP

(57) ABSTRACT

A system comprises a substrate having a plurality of apertures, and a clip. The clip is removably coupled to one of the plurality of apertures. The clip has a body, a plurality of fingers, a first leg, a second leg, a first notch, and a second notch. The fingers extend from the body to collectively form at least two tube-engaging regions. The first leg is adjacent to a first end of the body and extends from the body opposite the fingers. The second leg is adjacent to a second end of the body and extends from the body opposite the fingers. The first notch is adjacent to the first end of the body and is configured to receive a first portion of the substrate. The (Continued)

second notch is adjacent to the second end of the body and is configured to receive a second portion of the substrate.

20 Claims, 8 Drawing Sheets

(51) Int. Cl.
*A61B 50/22* (2016.01)
*F16L 3/223* (2006.01)

(56) References Cited

U.S. PATENT DOCUMENTS

| | | | | |
|---|---|---|---|---|
| 3,751,575 A * | 8/1973 | Barb | ............... | H04Q 1/142 248/222.12 |
| 4,244,544 A * | 1/1981 | Kornat | ............... | F16L 3/13 248/68.1 |
| 4,467,987 A * | 8/1984 | Small | ............... | F16L 3/223 248/68.1 |
| 5,027,478 A * | 7/1991 | Suhr | ............... | F16L 3/223 24/339 |
| 5,215,726 A * | 6/1993 | Kudla | ............... | A61L 2/26 206/370 |
| 5,309,604 A * | 5/1994 | Poulsen | ............... | F16L 3/223 24/339 |
| 5,384,103 A * | 1/1995 | Miller | ............... | A61L 2/26 206/508 |
| 6,244,447 B1 * | 6/2001 | Frieze | ............... | A61L 2/26 206/370 |
| 6,382,575 B1 * | 5/2002 | Frush | ............... | A61L 2/26 211/85.13 |
| 6,405,414 B1 * | 6/2002 | Byrnes | ............... | A61M 25/00 24/339 |
| 6,629,615 B2 * | 10/2003 | Kim | ............... | F16L 3/223 211/85.13 |
| 7,334,678 B2 * | 2/2008 | Kesler | ............... | A61M 25/002 206/364 |
| 7,533,852 B2 * | 5/2009 | Stigler | ............... | F16L 3/223 248/65 |
| 7,600,725 B2 * | 10/2009 | Mizukoshi | ............... | F16L 3/127 248/74.1 |
| 7,640,714 B2 * | 1/2010 | Waller | ............... | A61M 25/002 53/430 |
| 7,712,709 B2 * | 5/2010 | Winchester | ............... | F16L 3/223 248/89 |
| 7,886,906 B1 * | 2/2011 | Dunn | ............... | A61M 25/09 206/53 |
| 8,069,998 B2 * | 12/2011 | Thomas | ............... | A61B 50/34 206/370 |
| 8,998,151 B2 * | 4/2015 | Hoek | ............... | H02G 3/32 248/68.1 |
| 9,067,040 B2 * | 6/2015 | Byrnes | ............... | A61M 25/0023 |
| 9,534,708 B2 * | 1/2017 | Cripps, II | ............... | F16L 3/221 |
| 9,541,223 B2 * | 1/2017 | Meyers | ............... | F16L 55/035 |
| 9,920,858 B2 * | 3/2018 | Harnetiaux | ............... | F16L 3/223 |
| 9,951,888 B2 * | 4/2018 | Boriack | ............... | F16L 3/13 |
| 10,052,455 B1 * | 8/2018 | Anderson | ............... | A61B 50/20 |
| 10,391,190 B1 * | 8/2019 | Oko | ............... | F16B 5/0614 |
| 10,823,923 B2 * | 11/2020 | Chu | ............... | A61M 25/002 |
| 10,980,971 B2 * | 4/2021 | Huang | ............... | A61M 25/09 |
| 11,033,711 B2 * | 6/2021 | Coatsworth | ............... | A61B 90/90 |
| 11,090,127 B2 * | 8/2021 | Oko | ............... | A61B 50/33 |
| 2004/0118982 A1 * | 6/2004 | Shillings | ............... | F16L 3/223 248/68.1 |
| 2005/0006534 A1 * | 1/2005 | Shillings | ............... | F16L 3/223 248/68.1 |
| 2005/0061698 A1 * | 3/2005 | Delaney | ............... | A61M 25/002 206/364 |
| 2005/0077436 A1 * | 4/2005 | Nelson | ............... | F16L 3/223 248/68.1 |
| 2006/0237597 A1 * | 10/2006 | D'Andria | ............... | F16L 3/223 248/51 |
| 2007/0205123 A1 | 9/2007 | Bettenhausen | | |
| 2008/0314789 A1 | 12/2008 | Thomas | | |
| 2010/0006709 A1 | 1/2010 | Bleus | | |
| 2010/0132979 A1 * | 6/2010 | Chen | ............... | H02G 3/32 174/135 |
| 2012/0022470 A1 * | 1/2012 | Kuniyasu | ............... | A61M 25/002 604/265 |
| 2012/0037525 A1 * | 2/2012 | Peck | ............... | A61L 2/206 206/363 |
| 2014/0144798 A1 | 5/2014 | Benesh | | |
| 2015/0034776 A1 * | 2/2015 | St.John | ............... | F16L 3/223 248/68.1 |
| 2015/0094693 A1 | 4/2015 | Suzuki | | |
| 2015/0246202 A1 * | 9/2015 | Mcnamara | ............... | A61B 50/30 206/364 |
| 2017/0219126 A1 * | 8/2017 | Kato | ............... | B60R 16/08 |
| 2019/0260144 A1 * | 8/2019 | Pfeiffer-Wagner | .... | H01R 41/00 |
| 2019/0262577 A1 * | 8/2019 | Anderson | ............... | A61B 1/0014 |
| 2020/0080664 A1 * | 3/2020 | Perry | ............... | F16L 3/18 |
| 2021/0244904 A1 * | 8/2021 | Perrie | ............... | A61M 16/0497 |
| 2021/0386499 A1 * | 12/2021 | Bailey | ............... | A61B 50/33 |

FOREIGN PATENT DOCUMENTS

| | | | | |
|---|---|---|---|---|
| FR | 2907661 A1 * | 5/2008 | ............ | A61B 50/33 |
| GB | 717809 A * | 11/1954 | | |
| GB | 884297 A * | 12/1961 | | |
| GB | 1135702 A * | 12/1968 | | |
| JP | 2909889 B2 * | 6/1999 | | |
| JP | 3696692 B2 * | 9/2005 | ............ | F16L 3/223 |
| JP | 4264297 B2 * | 5/2009 | ............ | F16L 3/223 |
| JP | 4704180 B2 * | 6/2011 | ............ | F16L 3/223 |
| WO | WO-2020041132 A1 * | 2/2020 | ............ | B60T 17/046 |

OTHER PUBLICATIONS

International Preliminary Report on Patentability in corresponding International Application No. PCT/US2020/050250, mailed Nov. 8, 2021 (25 pages).

* cited by examiner

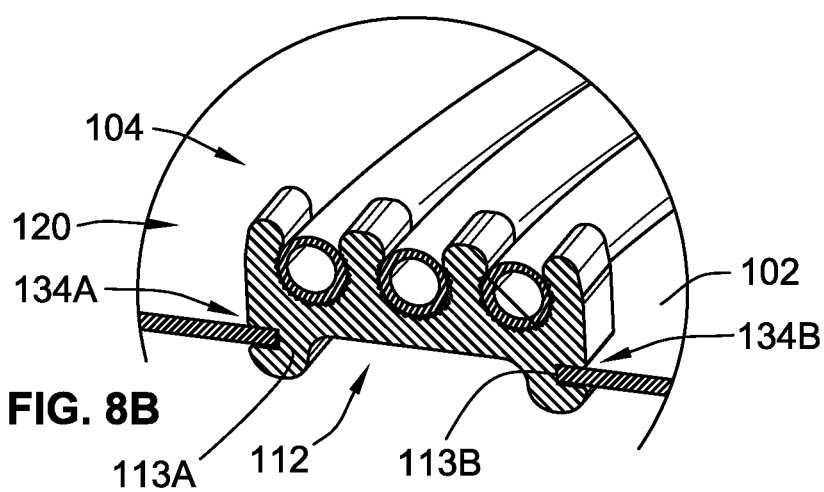
FIG. 8B
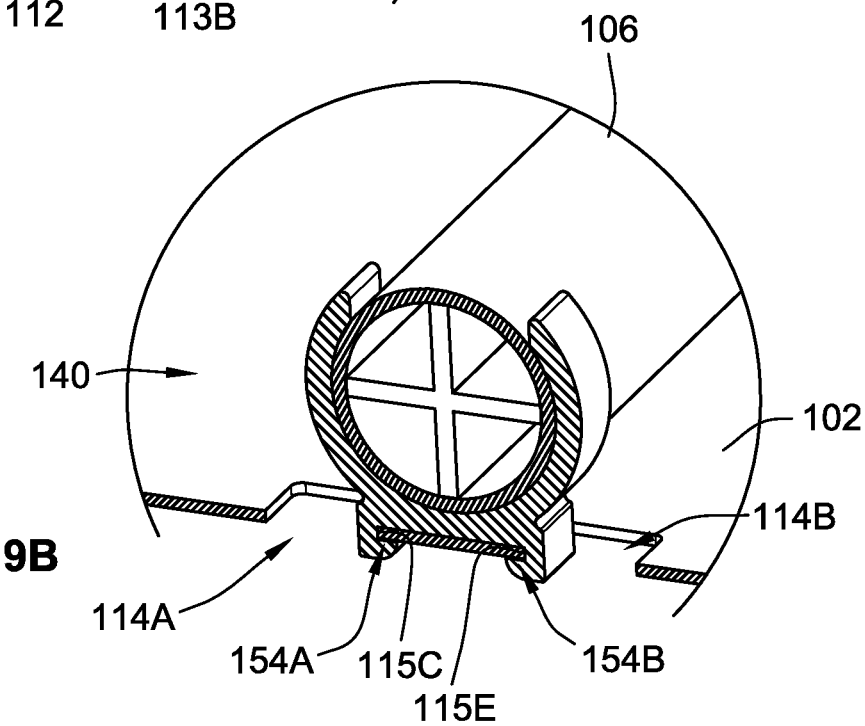
FIG. 9B
FIG. 10B
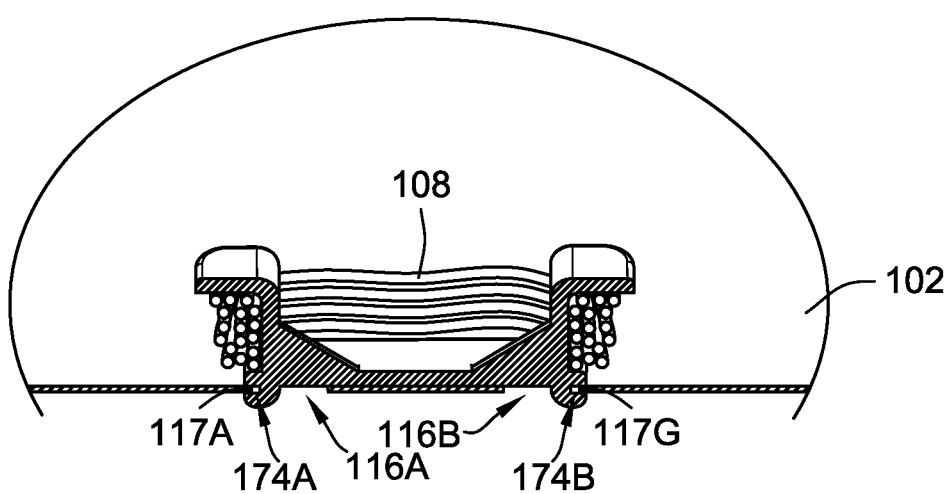

SYSTEMS AND METHODS FOR SECURING MEDICAL DEVICES

CROSS-REFERENCE TO RELATED APPLICATIONS

This application is a U.S. National Stage of International Application No. PCT/US2020/050250, filed Sep. 10, 2020, which claims the benefit of U.S. Provisional Patent Application No. 62/898,840, filed on Sep. 11, 2019, each of which is hereby incorporated by reference in its entirety.

TECHNICAL FIELD

The present disclosure relates generally to systems and methods for securing medical devices, and more particularly, to systems and methods for removably coupling clips to apertures in a substrate.

BACKGROUND

Components required for medical or surgical applications are often shipped together in one package. The various components can be coupled to a backing card, which can prevent the movement of the components during shipping and potential damage to the components. However, the backing cards are often designed for specific applications, and thus cannot be used for other applications if such a need should arise. Thus, new systems and methods for coupling components to backing cards are needed.

SUMMARY

According to aspects of the present disclosure, a system comprises a substrate and a clip. The substrate has a plurality of apertures defined therein. The clip is configured to be removably coupled to one of the plurality of apertures. The clip has a body, a plurality of fingers, a first leg, a second leg, a first notch, and a second notch. The fingers extend from the body generally in a first direction to collectively form at least two tube-engaging regions. The first leg is adjacent to a first end of the body and extends from the body in a second direction that is opposite the first direction. The second leg is adjacent to a second opposing end of the body and extends from the body generally in the second direction. The first notch is adjacent to the first end of the body and is configured to receive a first portion of the substrate therein. The second notch is adjacent to the second end of the body and is configured to receive a second portion of the substrate therein.

In some implementations, the first notch is defined in the first leg, and the second notch is defined in the second leg. In some implementations, the system includes a tube coupled to the substrate via the clip, such that (i) a first portion of the tube is positioned within a first one of the at least two tube-engaging regions and (ii) a second portion of the tube is positioned within a second one of the at least two tube-engaging regions.

In some implementations, the substrate includes a second plurality of apertures and a tool-clip. Each of the second plurality of apertures is positioned generally within a shape formed by the first plurality of apertures. The tool-clip includes a tool-clip body, a pair of curved fingers, a first leg, a second leg, a first tool-clip notch, and a second tool-clip notch. The pair of curved fingers extend from the tool-clip body generally in the first direction to form a tool-engaging region. The first leg is adjacent to a first end of the tool-clip body, and extends from the tool-clip body generally in the second direction. The second leg is adjacent to a second opposing end of the tool-clip body, extends from the body generally in the second direction. The first tool-clip notch is adjacent to the first end of the tool-clip body, and is configured to receive a third portion of the substrate therein. The second tool-clip notch is adjacent to the second end of the tool-clip body, and is configured to receive a fourth portion of the substrate therein.

In some implementations, the tool clip is configured to be removably coupled to the substrate by engaging a first one of the second plurality of apertures and a second one of the second plurality of apertures at the same time. In some implementations, the tool-clip is configured to engage an inner edge of the first one of the second plurality of apertures and an inner edge of the second one of the second plurality of apertures at the same time. In some implementations, the tool-clip is configured to engage an outer edge of the first one of the second plurality of apertures and an outer edge of the second one of the second plurality of apertures at the same time.

The above summary is not intended to represent each embodiment or every aspect of the present invention. Additional features and benefits of the present invention are apparent from the detailed description and figures set forth below.

BRIEF DESCRIPTION OF THE DRAWINGS

FIG. 8B is perspective view of the clip and the tube of FIG. 8A, after the clip is coupled to an aperture in a substrate, according to aspects of the present disclosure.

FIG. 9B is perspective view of the clip and the syringe of FIG. 9A, after the clip is coupled to two apertures in a substrate, according to aspects of the present disclosure.

FIG. 10B is perspective view of the clip and the electrical cable of FIG. 10A, after the clip is coupled to two apertures in a substrate, according to aspects of the present disclosure.

Figure 1:
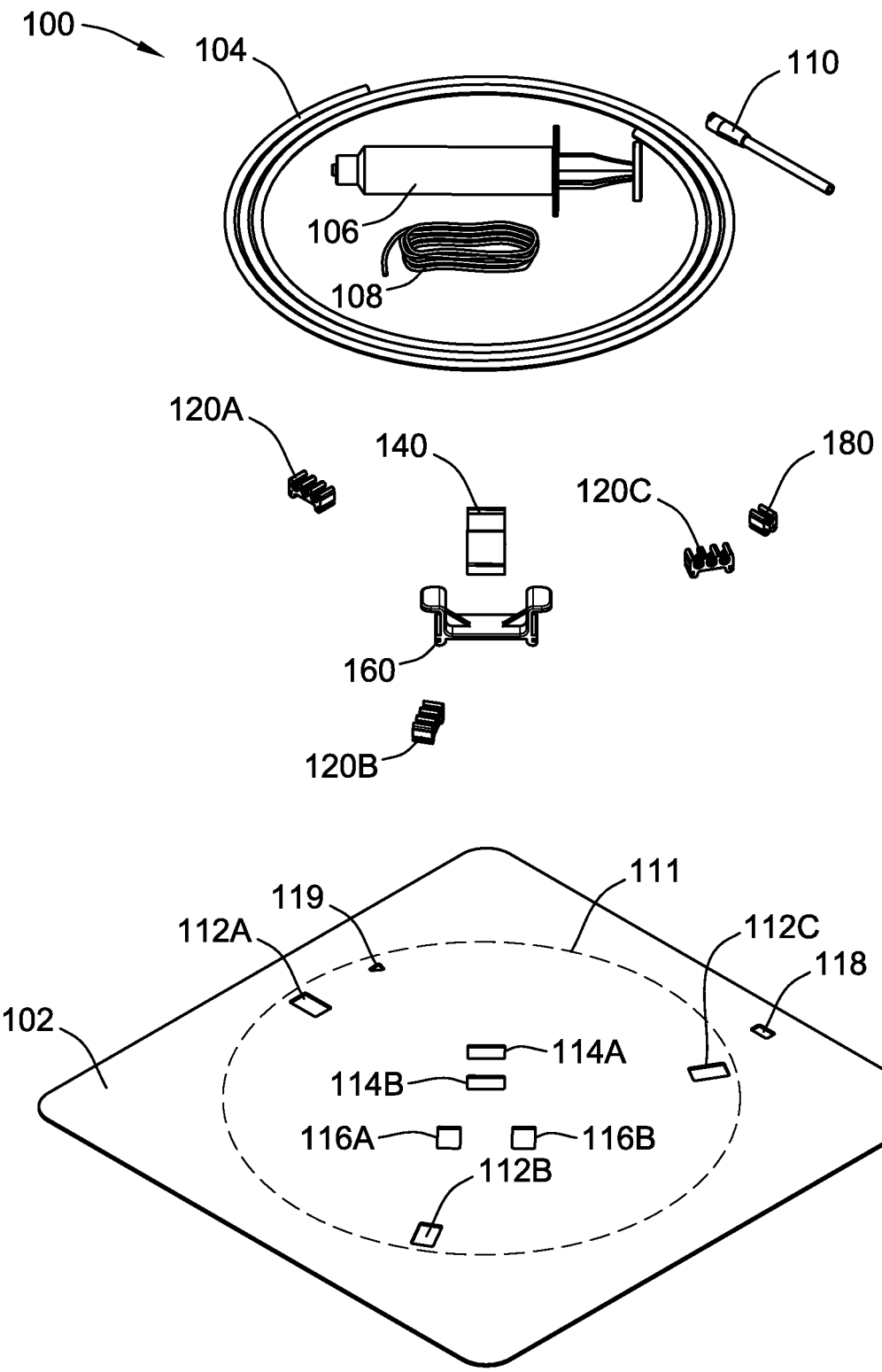
FIG. 1 is an exploded view of an example system that includes a substrate and a plurality of components coupled to the substrate, according to aspects of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Aspects of the present disclosure related to a medical device management system. The medical device management system generally includes a backing card that is configured to hold any number of different medical devices, such as a guidewire, a catheter, a syringe, an introducer needle, an electrical cable, an optical device, dispenser tubing, a laser, a cutter, a welder, etc.

FIG. 1 shows an exploded view of an exemplary medical device management system 100 that includes a substrate 102 (e.g., a backing card), a tube 104, a syringe 106, an electrical cable 108, and a needle 110 (which can be a guidewire introducer needle). The tube 104, the syringe 106, the electrical cable 108, and the needle 110 can be coupled to the substrate 102. In some implementations, the substrate 102 is made from a material that is flexible and/or bendable, such as a plastic material, a metal material, a paper material, polyethylene (such as high density polyethylene, or HDP), polypropylene, solid bleached sulphate (SBS) board, paperboard, cardboard, or any combination thereof. Other materials can also be used for the substrate 102.

In some implementations, the tube 104 is a lubricious medical tube that can be used as a protective dispenser tubing for guidewire. In certain medical applications, a length of guidewire can be inserted into and dispensed from the tube 104, and inserted into a desired area of a patient's body. In the illustrated implementation, the tube 104 is arranged in a generally circular, coiled shape, which enables the guidewire to be dispensed from the tube 104 with minimal force. Once the guidewire has been dispensed from the tube 104, the syringe 106, the electrical cable 108, and the needle 110 can be used for the desired application.

In other implementations, the tube 104 can have non-circular shapes. For example, the tube 104 could have an oblong shape (e.g., shaped like an egg), a racetrack shape (e.g., rounded on the ends with straight portions joining the rounded ends), or other shapes. In some implementations, the shape of the tube 104 on the substrate 102 is designed to fit a desired shape for packing and transporting the system 100.

The system 100 includes a plurality of apertures and a plurality of clips that can be used to maintain the tube 104 in the coiled shape, and to hold various other components of the system. Each of plurality of apertures is defined in the substrate 102. The plurality of apertures includes apertures 112A, 112B, and 112C; apertures 114A and 114B; apertures 116A and 116B; and aperture 118. In the illustrated implementations, each of these apertures has a generally rectangular shape with rounded corners. The substrate 102 can also include a triangular-shaped aperture 119. However, any of these apertures can have different shapes in other implementations. The apertures can be formed in the substrate 102 in a variety of different manners, including laser cutting, die cutting, stamping, injection molding, 3D printing, manual formation, removal of perforations, etc.

The apertures 112A, 112B, and 112C form a circular shape 111 on the surface of the substrate 102. In some implementations, the apertures 112A-112C are spaced evenly about the circumference of the circular shape 111, and are thus spaced apart by about 120°. Other implementations could include two apertures (spaced apart by about 180°), four apertures (spaced apart by about 90°), or other numbers of apertures. In still other implementations, the apertures 112A-112C are not spaced evenly about the circumference of the circular shape 111. These other implementations could also include more or less than three apertures not evenly spaced about the circumference of the circular shape 111. In further implementations, the apertures 112A-112C form a shape other than a circle on the surface of the substrate 102. In even further implementations, more or less than three apertures form a shape other than a circle on the surface of the substrate 102.

The apertures 114A, 114B, 116A, and 116B are positioned inside the circular shape 111 formed by the apertures 112A, 112B, and 112C. The aperture 118 is positioned outside the circular shape 111 formed by the apertures 112A, 112B, and 112C. The apertures 112A, 112B, and 112C are configured to receive clips 120A, 120B, and 120C, respectively. The apertures 114A and 114B are configured to receive clip 140. The apertures 116A and 116B are configured to receive clip 160. The aperture 118 is configured to receive clip 180. The aperture 119 can be used as an indicator, as is discussed in more detail herein.

Figure 2:
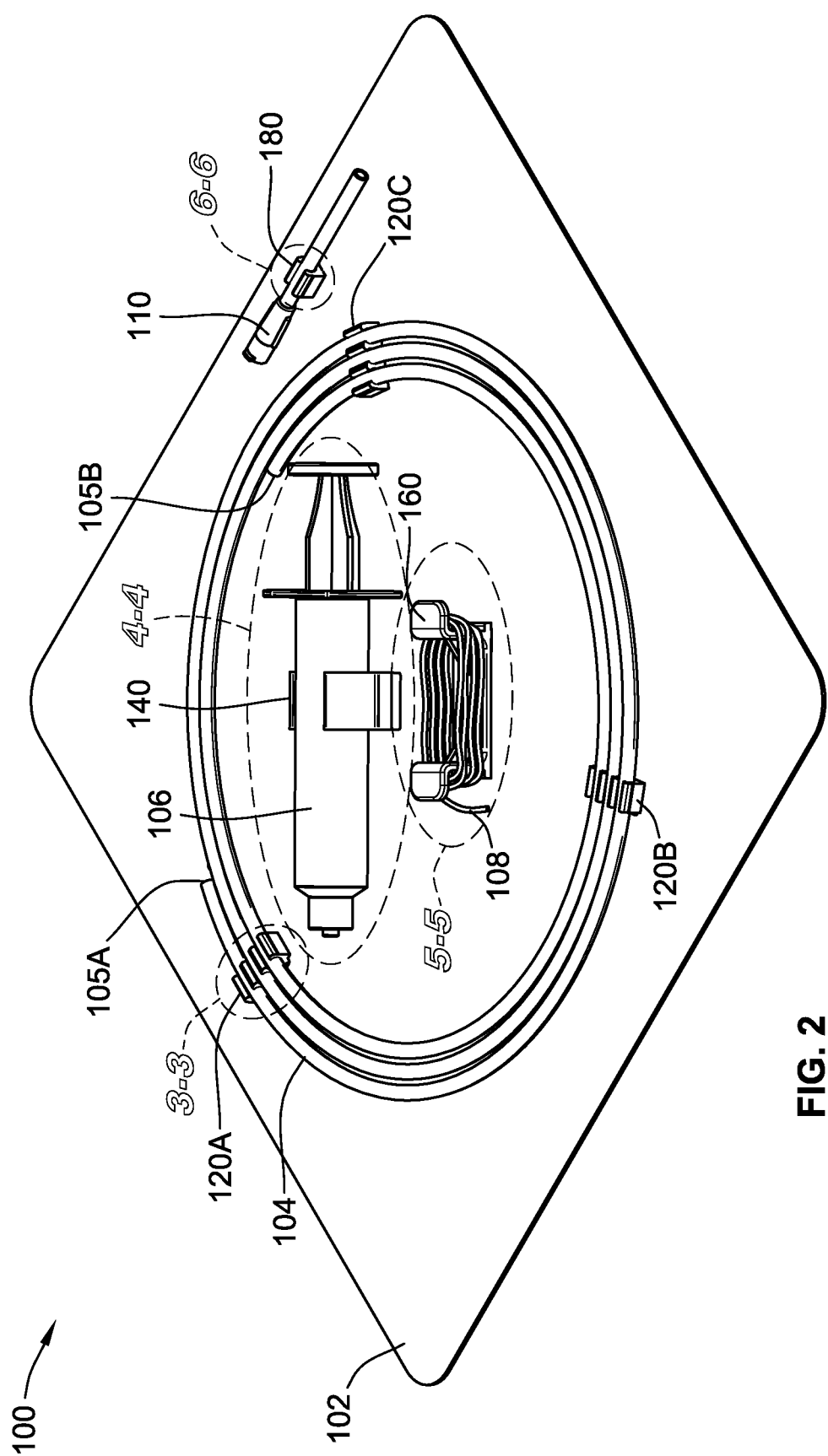
FIG. 2 is an assembled view of the system of FIG. 1, according to aspects of the present disclosure.

FIG. 2 shows an assembled view of system 100. The clips 120A, 120B, and 120C are coupled to the substrate 102, and thus arranged along the circular shape 111 (FIG. 1) that is formed on the surface of the substrate 102 by the apertures 112A, 112B, and 112C. Each of the clips 120A, 120B, and 120C is also coupled to multiple portions of the tube 104. End 105A of the tube 104 is coupled to an outer portion of the clip 120A. The tube 104 continues in its coiled shape, with various portions of the tube 104 coupled to outer portions of the clips 120B and 120C. The tube 104 then continues back around to clip 120A, where a portion of the tube 104 is coupled to a middle portion of the clip 120A. The coupling between the tube 104 and the clips 120A, 120B, and 120C continues in this manner, until an opposing end 105B of the tube 104 is coupled to an inner portion of the clip 120C. Thus, the clips 120A, 120B, and 120C aid in maintaining the tube 104 in the generally circular, coiled shape.

Clip 140 is coupled to the substrate 102 inside the circular shape 111 that is formed on the surface of the substrate 102 by the apertures 112A, 112B, and 112C. Clip 140 is also coupled to the syringe 106, which is thus also positioned inside the circular shape 111 of the apertures 112A, 112B, and 112C. Clip 160 is similarly coupled to the substrate 102 inside the circular shape 111 that is formed on the surface of the substrate 102 by the apertures 112A, 112B, and 112C. Clip 160 is also coupled to the electrical cable 108, which is thus also positioned inside the circular shape 111 of the apertures 112A, 112B, 112C. Finally, clip 180 is coupled to the substrate 102 outside of the circular shape 111 of the apertures 112A, 112B, and 112C. Clip 180 is coupled to the needle 110, which is thus also positioned outside the circular shape 111 of the apertures 112A, 112B, and 112C. The triangular-shaped aperture 119 points toward end 105A of the tube 104, indicating to a user of the system 100 where the guidewire should be initially inserted into the tube 104.

Figure 3:
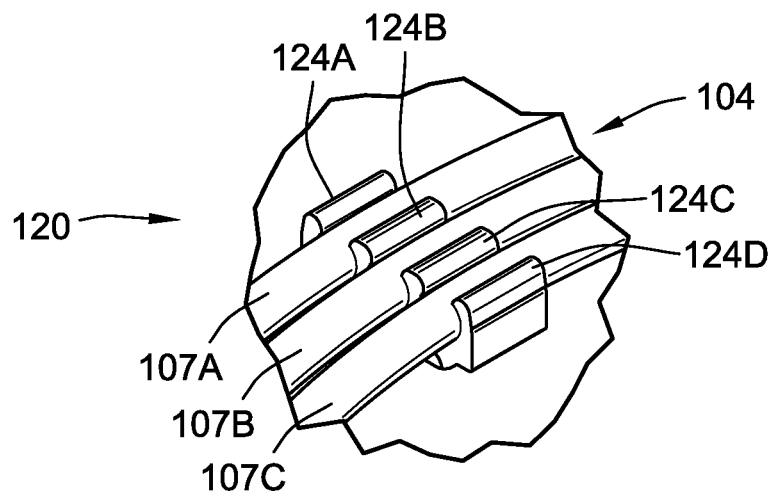
FIG. 3 is a perspective view of a clip of the system of FIG. 1, and a tube coupled to the clip, according to aspects of the present disclosure.
Figure 4:
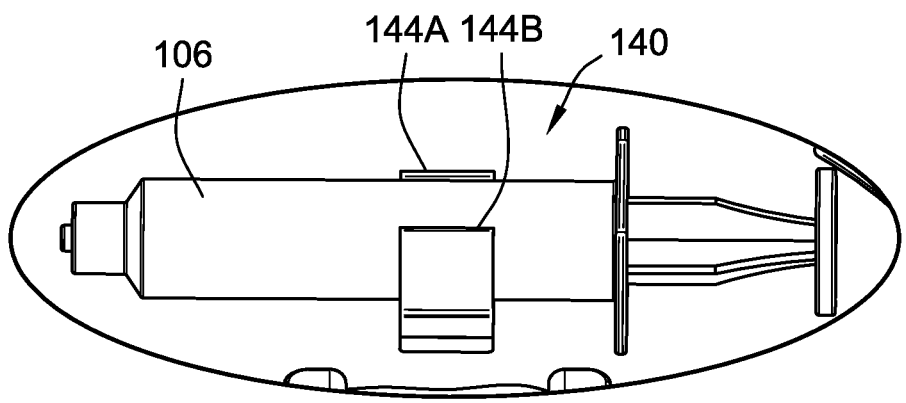
FIG. 4 is a perspective view of a clip of the system of FIG. 1, and a syringe coupled to the clip, according to aspects of the present disclosure.
Figure 5:
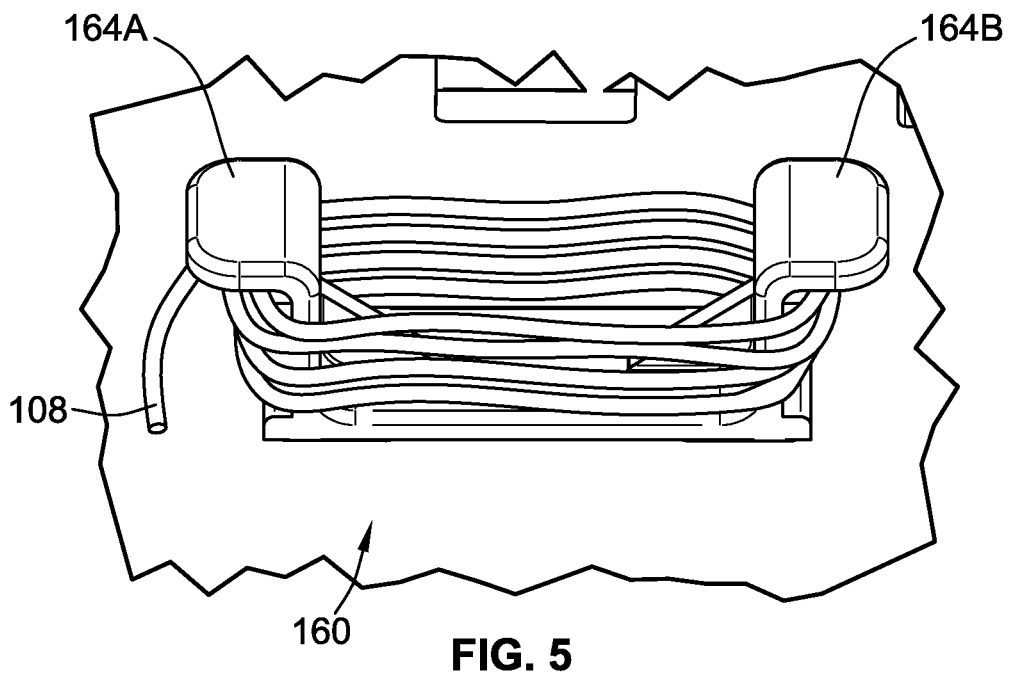
FIG. 5 is a perspective view of a clip of the system of FIG. 1, and an electrical cable coupled to the clip, according to aspects of the present disclosure.
Figure 6:
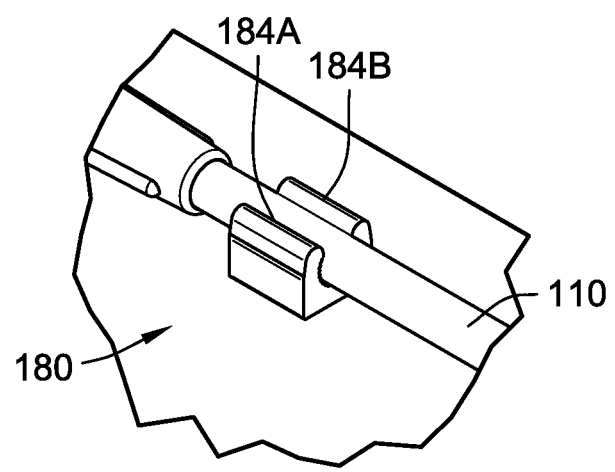
FIG. 6 is a perspective view of a clip of the system of FIG. 1, and a needle coupled to the clip, according to aspects of the present disclosure.

FIG. 3 shows a zoomed-in views of the tube 104 and the clip 120A. As is shown, the clip 120 includes multiple fingers 124A, 124B, 124C, and 124D forming regions that engage different portions of the tube 104. Fingers 124A and 124B form an outer region of the clip 120 engages portion 107A of the tube 104. Fingers 124B and 124C form a middle region of the clip 120 engages portion 107B of the tube 104. Fingers 124C and 124D form an inner region of the clip 120 engages portion 107C of the tube 104. FIG. 4 shows a zoomed-in view of the syringe 106 and the clip 140. The clip 140 includes fingers 144A and 144B forming a single region that engages the syringe 106. FIG. 5 shows a zoomed-in view of the electrical cable 108 and the clip 160. The electrical cable 108 is wrapped around fingers 164A and 164B of the clip 160. Finally, FIG. 6 shows a zoomed-in view of the needle 110 and the clip 180. The clip 180 includes fingers 184A and 184B forming a single region that engages the needle 110.

Figure 7A:
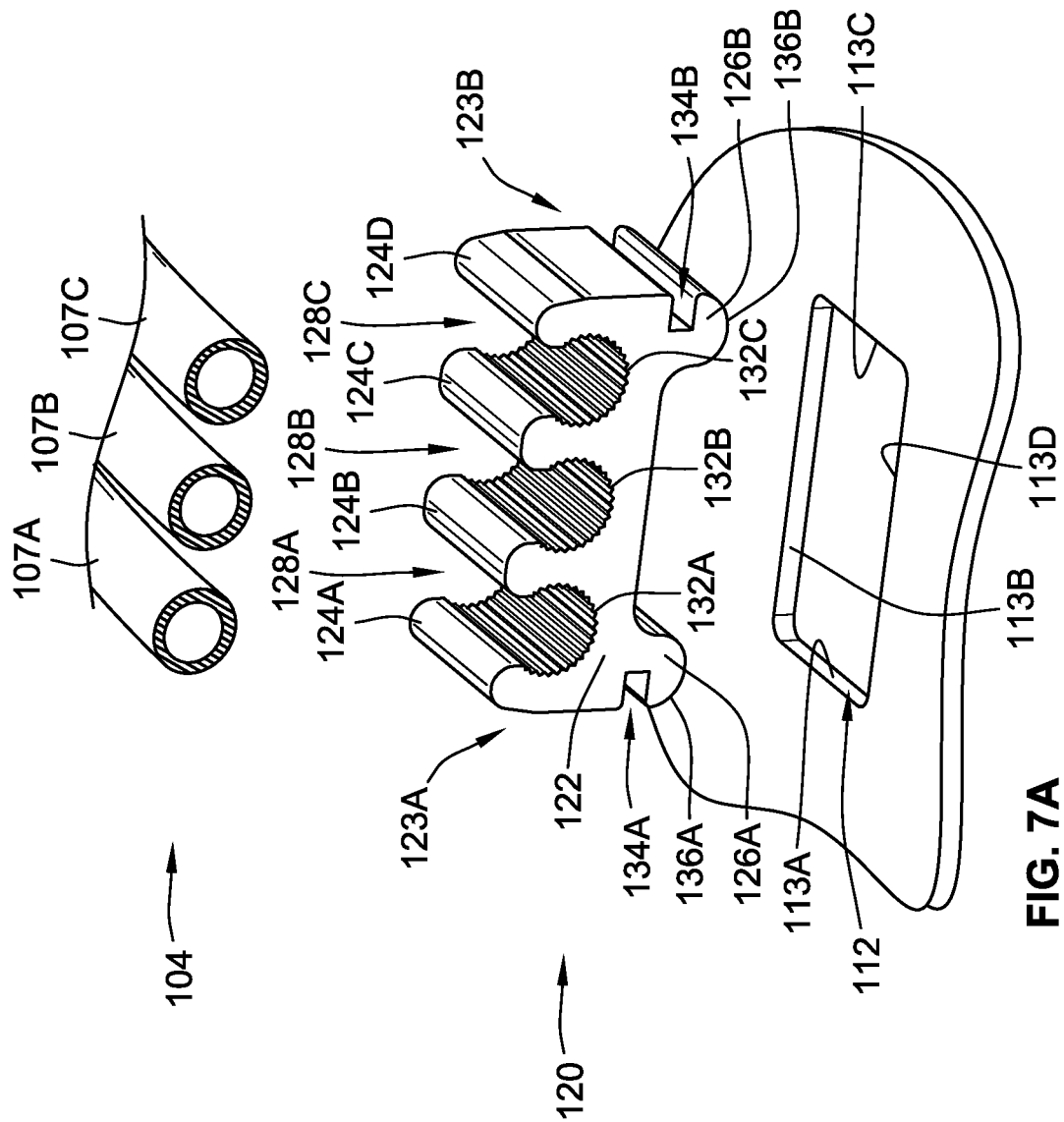
FIG. 7A is perspective view of the clip and the tube of FIG. 3, prior to the tube being coupled to the clip, according to aspects of the present disclosure.
Figure 7B:
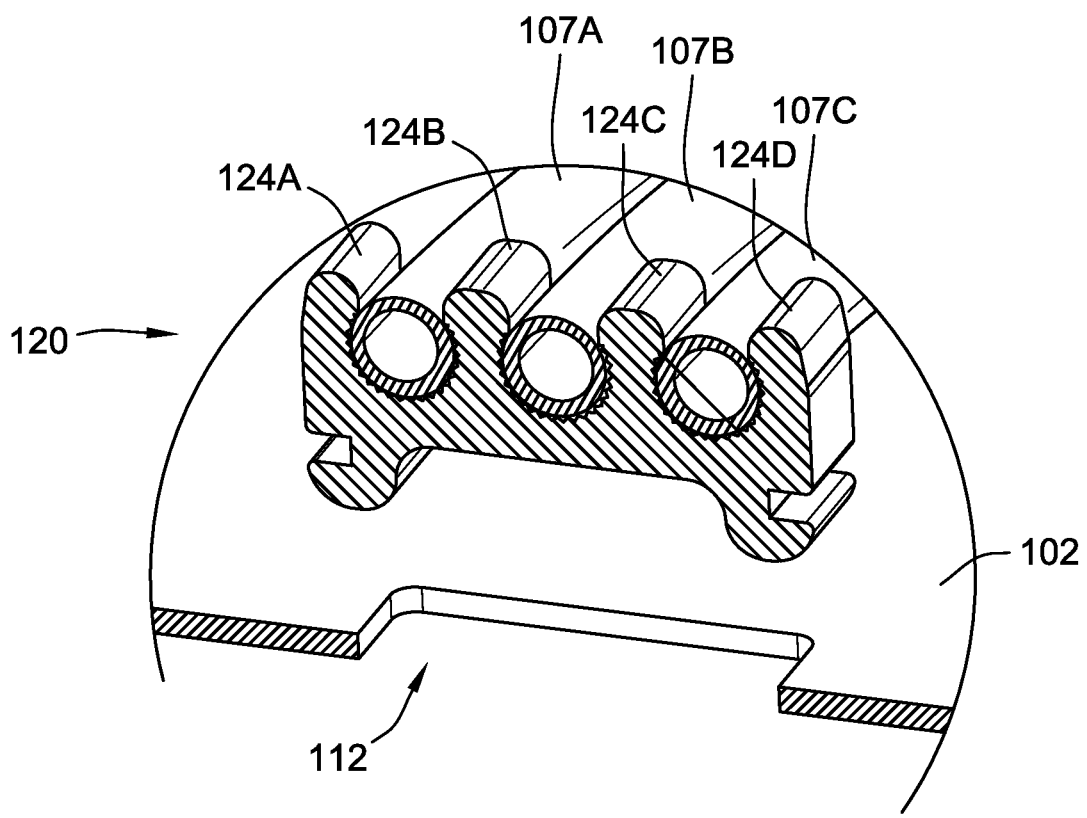
FIG. 7B is perspective view of the clip and the tube of FIG. 7A after the tube is coupled to the clip, according to aspects of the present disclosure.
Figure 7C:
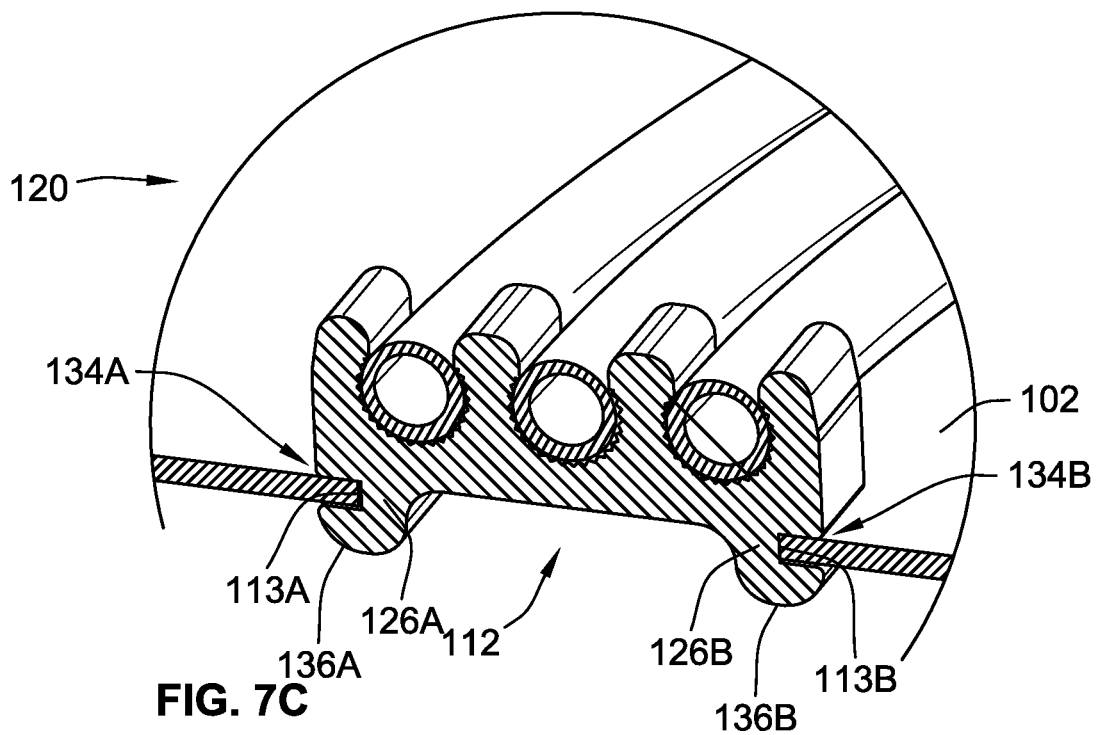
FIG. 7C is perspective view of the clip and the tube of FIG. 7A, after the clip is coupled to an aperture, according to aspects of the present disclosure.

FIGS. 7A-7C show how clip 120 (which could be any of clips 120A, 120B, or 120C, or another similar clip) engages the tube 104 and is removably coupled to an aperture 112 (which could be any of apertures 112A, 112B, or 112C, or another similar aperture). In FIG. 7A, the clip 120 is not coupled to the aperture 112 defined in the substrate 102, and has not engaged the tube 104. Edges 113A, 113B, 113C, and 113D of the substrate 102 form the periphery of the aperture 112. For viewing purposed, edge 113D of the substrate 102 is not shown in FIGS. 7B and 7C.

The clip 120 is formed from a body 122; fingers 124A, 124B, 124C, and 124D; a first leg 126A; and a second leg 126B. The fingers 124A-124D each extend away from the body generally in a first direction, while the first leg 126A and the second leg 126B each extend away from the body generally in a second direction that is opposite the first direction. The fingers 124A-124D are generally spaced across the entire length of the clip 120 between a first end 123A and a second end 123B. The first leg 126A is positioned adjacent to the first end 123A, while the second leg 126B is positioned adjacent to the second end 123B.

Together, the fingers 124A-124D form a plurality of tube-engaging regions. The tube-engaging regions are generally the open spaces between adjacent fingers that are configured to receive portions of the tube 104. Fingers 124A and 124B form a tube-engaging region 128A. Fingers 124B and 124C form a tube-engaging region 128C. Fingers 124C and 124D form a tube-engaging region 128C. Each of the tube-engaging regions 128A-128C has a respective open inlet area formed between adjacent pairs of the fingers 124A-124D. The inlet areas form the open portion of the tube-engaging regions 128A-128C.

Each of the inlet areas is positioned opposite the body (e.g., nearer to the fingers 124A-124D than the legs 126A and 126B). In the illustrated implementation, each of the tube-engaging regions 128A-128C has a generally circular cross-section except for the respective inlet areas. Thus, each of the tube-engaging regions 128A-128C has a generally C-shaped cross section. However, the tube-engaging regions 128A-128C can have other shapes as well.

Each of the tube-engaging regions 128A-128C also includes a respective set of teeth that extend from the surface of the clip 120 within the tube-engaging regions 128A-128C. Tube-engaging region 128A includes a set of teeth 132A. Tube-engaging region 128B includes a set of teeth 132B. Tube-engaging region 128C includes a set of teeth 132C. The sets of teeth 132A-132C are configured to contact the portions 107A-107C of the tube 104, to thereby aid in gripping the portions 107A-107C of the tube 104 when the portions 107A-107C are engaged by the tube-engaging regions 128A-128C.

The clip 120 further includes a first notch 134A and a second notch 134B that aid in removably coupling the clip 120 to the substrate 102. A terminus 136A of the first leg 126A curves outward away from the body 122 and the second leg 126B, such that the first notch 134A faces outward, and is defined by (i) the first leg 126A and (ii) the first end 123A of the body 122. A terminus 136B of the second leg 126B curves outward away from the body 122 and the first leg 126A, such that the second notch 134B faces outward, and is defined by (i) the second leg 126B and (ii) the second end 123B of the body 122. Thus, the first notch 134A is positioned adjacent to the end 123A of the body 122, and the second notch 134B is positioned adjacent to the end 123B of the body 122.

The notches 134A and 134B are configured to receive different portions of the substrate 102 therein, to thereby aid in removably coupling the clip 120 to the substrate 102. In some implementations, both of the notches 134A and 134B have a generally U-shaped cross-section. The U-shaped cross-sections could have a flat base (as shown in the illustrated implementation, a curved base, a pointed base, or a base with another shape. However, the notches 134A and 134B can have cross-sections of other shapes as well.

In some implementations, the clip 120 is formed from a resilient material, such that the first leg 126A and the second leg 126B are resilient. In this manner, the first leg 126A and the second leg 126B can be temporarily deformed in response to force applied to the legs 126A and 126B (such as by the substrate 102), and then return to their original positions. In some implementations the clip 120 is formed from a plastic material, which could be resilient or non-resilient. In some implementations the clip 120 is monolithic, and the body 122, the fingers 124A-124D, and the legs 126A-126D are all formed from a single piece of material. In other implementations the clip 120 is not monolithic, and the various components of the clip 120 can be removably attached to each other to form the clip 120.

Referring now to FIG. 7B, the portions 107A-107C of the tube 104 can be positioned within the tube-engaging regions 128A-128C of the clip 120, to thereby couple the tube 104 to the clip 120. Portion 107A of the tube 104 is positioned within the tube-engaging region 128A that is formed by fingers 124A and 124B of the clip 120. Portion 107B of the tube 104 is positioned within the tube-engaging region 128B that is formed by fingers 124B and 124C of the clip 120. Portion 107C of the tube 104 is positioned within the tube-engaging region 128C that is formed by fingers 124C and 124D of the clip 120.

Referring now to FIG. 7C, the clip 120 can be inserted into the aperture 112, to thereby removably couple the clip 120 to the aperture 112. As the clip 120 is inserted into the aperture 112, edge 113A of the substrate 102 contacts the first leg 126A, while edge 113B of the substrate 102 contacts the second leg 126B. Because the legs 126A and 126B are resilient, this contact compresses the legs 126A and 126B inward toward each other. The edge 113A is thus able to slide along the curved terminus 136A of the first leg 126A, while the edge 113B is able to slide along the curved terminus 136B of the second leg 126B.

Once the clip 120 is inserted into the aperture 112 a sufficient amount, notch 134A receives the edge 113A, and notch 134B receives the edge 113B. The receiving of the edges 113A and 113B allows the legs 126A and 126B to decompress and return to their original positions. Thus, as shown in FIG. 7C, when the clip 120 is removably coupled to the aperture 112, the edge 113A of the substrate 102 is positioned between (i) the terminus 136A of the first leg 126A and (ii) the first end 123A of the body 122. Similarly, the edge 113B of the substrate 102 is positioned between (i) the terminus 136B of the second leg 126B and (ii) the second end 123B of the body 122. If force is applied to the clip 120 in an attempt to remove the clip 120 from the aperture 112, the edges 113A and 113B will simply press against the legs 126A and 126B, preventing the clip 120 from being removed. Generally, the legs 126A and 126B must be manually compressed inward to remove the clip 120, such that the notches 134A and 134B no longer receive the edges 113A, 113B of the substrate 102.

Figure 8A:
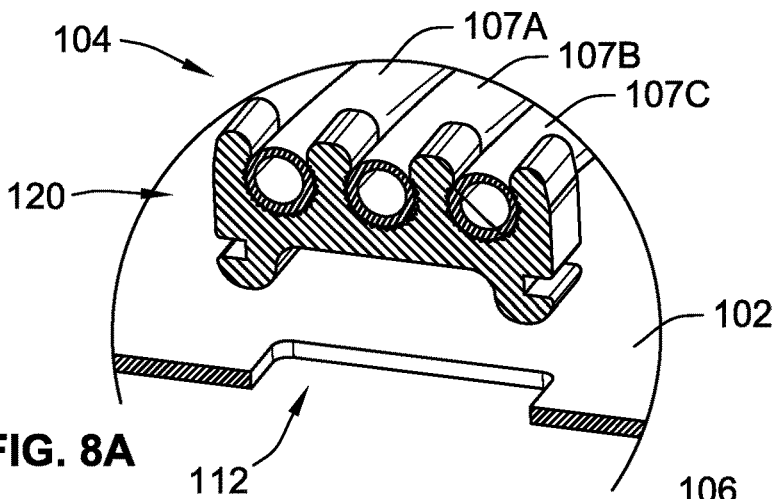
FIG. 8A is perspective view of the clip and the tube of FIG. 3, after the tube is coupled to the clip, according to aspects of the present disclosure.

While FIGS. 7B and 7C show the tube 104 being coupled to the clip 120 and the clip 120 then being coupled to the aperture 112, these steps can occur in reverse order. Thus, the clip 120 can be coupled to the aperture 112, and the tube 104 is then coupled to the clip 120 by inserting the portions 107A-107C of the tube 104 into the tube-engaging regions 128A-128C FIGS. 8A-10B illustrate comparisons of how the clips 120, 140, and 160 are all coupled to the various apertures defined in the substrate. FIG. 8A illustrates the portions 107A-107C of the tube 104 coupled to the clip 120 and positioned above aperture 112, as discussed above with respect to at least FIGS. 7A-7C.

Figure 9A:
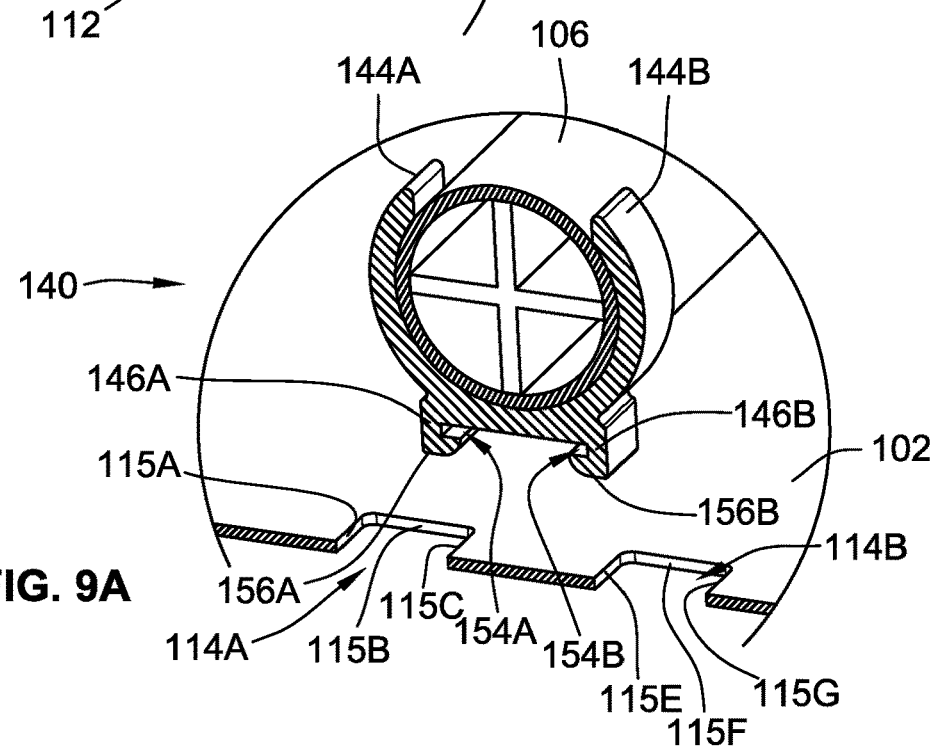
FIG. 9A is perspective view of the clip and the syringe of FIG. 4, after the syringe is coupled to the clip, according to aspects of the present disclosure.

FIG. 9A illustrates the syringe 106 coupled to clip 140. The syringe 106 and the clip 140 are positioned above apertures 114A and 114B defined in the substrate 102. Aperture 114A is defined by edges 115A, 115B, and 115C of the substrate 102. Aperture 114B is defined by edges 115D, 115E, and 115F of the substrate 102. Each of the apertures 114A and 114B are also defined by a fourth edge of the substrate 102, which not shown in FIGS. 9A and 9B for viewing purposes.

The clip 140 has a similar structure to clip 120, and includes a body 142, fingers 144A and 144B, and legs 146A and 146B. Fingers 144A and 144B extend away from the body 142 in a first direction and form a syringe-engaging region therebetween. The syringe-engaging region can have a circular cross-section apart from the open inlet area opposite the body 142 (e.g., a C-shaped cross-section). Legs 146A and 146B extend away from the body 142 in a second direction opposing the first direction. The terminus 156A of leg 146A curves inward toward leg 146B, and the terminus 156B of leg 146B curves inward toward leg 146A. A notch 154A is thus defined between (i) the terminus 156A of the leg 146A and (ii) a first end 143A of the body 142. Similarly, a notch 154B is defined between (i) the terminus 156B of the leg 146B and (ii) a second end 143B of the body 142. Notches 154A and 154B both face inwardly (e.g., toward each other). In some implementations, the notches 154A and 154B have U-shaped cross-sections, similar to notches 134A and 134B.

Figure 10A:
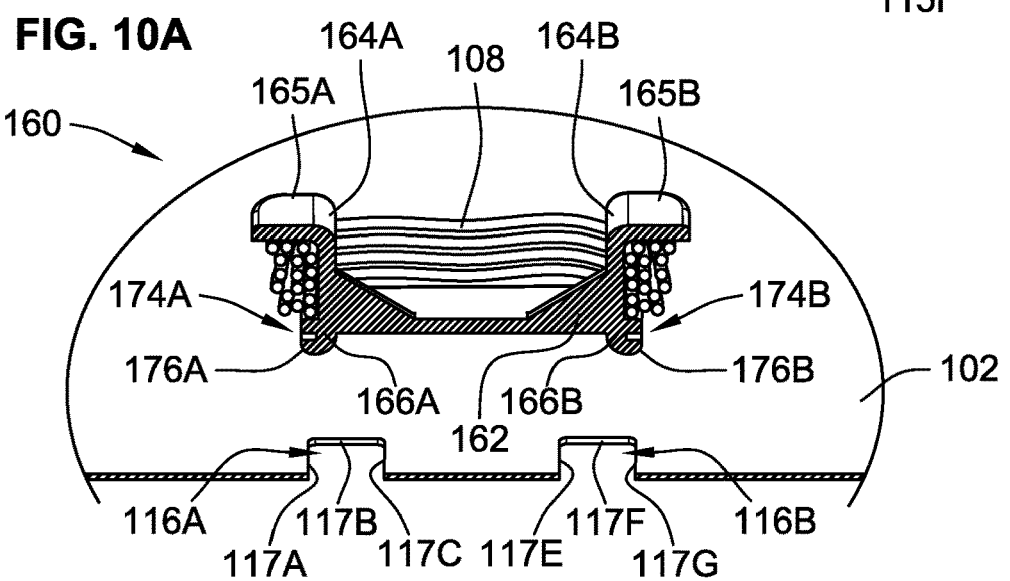
FIG. 10A is perspective view of the clip and the electrical cable of FIG. 5, after the electrical cable is coupled to the clip, according to aspects of the present disclosure.

FIG. 10A illustrates the electrical cable 108 coupled to clip 160. The electrical cable 108 and the clip 160 are positioned above apertures 116A and 116B defined in the substrate 102. Aperture 116A is defined by edges 117A, 117B, and 117C of the substrate 102. Aperture 116B is defined by edges 117D, 117E, and 117F of the substrate 102. Each of the apertures 116A and 116B are also defined by a fourth edge of the substrate 102, which not shown in FIGS. 10A and 10B for viewing purposes.

The clip 160 has a similar structure to clip 120, and includes a body 162, fingers 164A and 164B, and legs 166A and 166B. Fingers 164A and 164B extend away from the body 162 in a first direction, while legs 166A and 166B extend away from the body 162 in a second direction opposing the first direction. A terminus 165A of finger 164A extends away from finger 164B, while a terminus 165B of finger 164B extends away from finger 164A. Thus, fingers 164A and 164B form respective cable-engaging regions 168A and 168B thereunder. As shown, the electrical cable 108 is configured to be wrapped around the fingers 164A and 164B, to thereby couple the electrical cable 108 to the clip 160. The terminus 165A of finger 164A and the terminus 165B of the finger 164B prevent the electrical cable 108 from being inadvertently removed from the clip 160, without first being unwrapped from the fingers 164A and 164B.

The lower portion of the clip 160 is similar to the lower portion of the clip 120. The terminus 176A of leg 166A curves outward away from the body 162 and the leg 166B, and the terminus 176B of leg 166B curves outward away from the body 162 and the leg 166A. A notch 174A is defined between (i) the terminus 176A of the leg 166A and (ii) a first end 163A of the body 162. Similarly, a notch 174B is defined between (i) the terminus 176B of the leg 166B and (ii) a second end 163B of the body 162. Notches 174A and 174B both face outwardly (e.g., away from each other). In some implementations, the notches 174A and 174B have U-shaped cross-sections, similar to notches 134A and 134B.

FIGS. 8B, 9B, and 10B illustrates clips 120, 140, and 160 coupled to their respective apertures. In FIG. 8B, clip 120 is removably coupled to the edges of the substrate 102 that form the edges of the single aperture 112. The outwardly-facing notch 134A receives edge 113A therein, and the outwardly-facing notch 134B receives edge 113B therein.

In FIG. 9B, clip 140 is removably coupled to the edges of the substrate 102 that form the inner edges of two adjacent apertures 114A and 114B. The inner edge of each of the two adjacent apertures 114A and 114B is the edge of one of the apertures that is nearest to the other aperture. The inwardly-facing notch 154A receives edge 115C therein, and the inwardly-facing notch 154B receives edge 115D therein. Thus, while edges 115C and 115D of the substrate 102 form portions of the periphery of two different apertures 114A and 114B, both edges 115C and 115D are used to couple the clip 140 to the substrate 102.

In FIG. 10B, clip 160 is removably coupled to the edges of the substrate 102 that form the outer edges of two adjacent apertures 116A and 116B. The outer edge of each of the two adjacent apertures 116A and 116B is the edge of one of the apertures that is furthest from the other aperture. The outwardly-facing notch 174A receives edge 117A therein, and the outwardly-facing notch 174B receives edge 117F therein. Thus, while edges 117A and 117F of the substrate 102 form portions of the periphery of two different apertures 116A and 116B, both edges 117A and 117F are used to couple the clip 160 to the substrate 102.

While clips 120, 140, 160, and 180 are illustrated as being used to couple the tube 104, the syringe 106, the electrical cable 108, and the needle 110 to the substrate 102, any combination of clips can be used to couple any combination of components to the substrate 102. While the illustrated implementation is directed to a specific medical device management system that can be used to manage and dispense guidewire, other types of medical device management systems can be formed from the substrate 102, the various apertures, and the various clips. The apertures defined by the substrate 102 can have any number, size, shape, etc. The apertures can thus have any arrange and can be designed to engage any type of clip for holding any type of component.

For example, in one implementation, all of the apertures have the same size and shape, and all of the clips have identical legs and notches to couple the clips to the apertures. The fingers and the engaging regions can be selected for any application that requires any component to be coupled to the substrate 102. In another implementation, the substrate 102 may define different sets of apertures, where each set of apertures has a different size. In a further implementation, all of the apertures defined in the substrate 102 have the same size.

Thus, the substrate 102 can be custom-formed for any type of application that may require the use of any type of clip to couple any type of component to the substrate 102. The substrate 102 can include multiple sets of one or more apertures. One set of one or more apertures can include single apertures of which the outer edges are received by the clips. Another set of one or more apertures can include pairs of apertures of which the inner edges are received by the clips. Another set of one or more apertures can include pairs of apertures of which the outer edges are received by the clips. Any of these apertures can be positioned in any shape and in any location on the substrate 102.

Generally, clips configured to couple components other than the tube 104 (e.g., clips 140, 160, and 180) to the substrate 102 can be described as tool-clips that include one or more tool-engaging regions configured to engage portions of a tool (which could be the syringe, electrical cable, needle, or other components), and one or more tool-clip notches configured to receive portions of the substrate that form the edges of various apertures. In some implementations, the tool-engaging regions include the space between adjacent fingers, into which the tool can be inserted. In other implementations, the tool-engaging regions include spaces underneath the terminus of at least two fingers, around which the tool is wrapped.

Generally, clips configured to couple components to the substrate 102 can be described as clips that include one or more component-engaging regions configured to engage portions of a component (which could be the tube, syringe, electrical cable, needle, or other components), and one or more notches configured to receive portions of the substrate that form the edges of various apertures. In some implementations, the component-engaging regions include the space between adjacent fingers, into which the component can be inserted. In other implementations, the component-engaging regions include spaces underneath the terminus of at least two fingers, around which the component is wrapped.

Different features of the different clips discussed herein can be combined as needed for different applications. In one example, a clip includes outwardly-facing notches to receive the edges of a single aperture, and two or more fingers that form component-engaging regions configured to receive a portion of a component. In another example, a clip includes outwardly-facing notches to receive the edges of a single aperture, and one or more fingers around which a portion of a component can be wrapped.

In a further example, a clip includes inwardly-facing notches to receive the inner edges of two different apertures, and two or more fingers that form component-engaging regions configured to receive a portion of a component. In an additional example, a clip includes inwardly-facing notches to receive the inner edges of two different apertures, and one or more fingers around which a portion of a component can be wrapped.

In still another example, a clip includes outwardly-facing notches to receive the outer edges of two different apertures, and two or more fingers that form component-engaging regions configured to receive a portion of a component. In an even further example, a clip includes outwardly-facing notches to receive the edges of two different apertures, and one or more fingers around which a portion of a component can be wrapped.

In an additional example, features from different clips can be combined. A clip in this example could have at least two fingers that define a component-engaging region therebetween. The terminus of each of the fingers could extend outwardly away from each other, such that a component could also be wrapped around the at least two fingers. A clip in this example could also include one inwardly-facing notch configured to receive a portion of the substrate forming the inner edge of an aperture, and an outwardly-facing notch configured to receive a portion of the substrate forming the outer of an adjacent aperture.

One or more elements or aspects or steps, or any portion (s) thereof, from one or more of any of claims 1-26 below can be combined with one or more elements or aspects or steps, or any portion(s) thereof, from one or more of any of the other claims 1-26 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system comprising:
   a substrate having a first plurality of apertures and a second plurality of apertures defined therein, the first plurality of apertures including a first aperture, a second aperture and a third aperture arranged to form a circular shape on a surface of the substrate, the second plurality of apertures including a fourth aperture and a fifth aperture positioned inside the circular shape; and
   a plurality of clips including a first clip, a second clip, and a third clip removably coupled to the first aperture, the second aperture, and the third aperture respectively; and
   a fourth clip removably coupled to the fourth aperture and the fifth aperture;
   wherein each of the first clip, second clip, and third clip comprise:
      a body,
      a plurality of fingers extending from the body generally in a first direction to collectively form at least two tube-engaging regions,
      a first leg adjacent to a first end of the body that extends from the body generally in a second direction that is opposite the first direction, the first leg having a curved terminus to aid the clip in engaging a first edge of one aperture of the first aperture, the second aperture, or the third aperture, a second leg adjacent to a second opposing end of the body that extends from the body generally in the second direction the second leg having a curved terminus to aid the clip in engaging a second edge of the one aperture of the first aperture, the second aperture, or the third aperture, a first notch defined by the first leg such that the first notch is positioned between the first end of the body and the curved terminus of the first leg, the first notch facing away from the second leg, the first notch being configured to receive the first edge of the one aperture of the first aperture, the second aperture, or the third aperture, and a second notch defined by the second leg such that the second notch is positioned between the second end of the body and the curved terminus of the second leg, the second notch facing away from the first leg, the second notch being configured to receive the second edge of the one aperture of the first aperture, the second aperture, or the third aperture; and wherein the fourth clip comprises:
a body,
a first finger and a second finger extending in the first direction to form a syringe-engaging region therebetween,
a first leg of the fourth clip and a second leg of the fourth clip extending in the second direction, a first terminus adjacent to the first leg of the fourth clip and a second terminus adjacent to the second leg of the fourth clip,
a first notch of the fourth clip defined between the first terminus of the first leg of the fourth clip and a first end of the body, and
a second notch of the fourth clip defined between the second terminus of the second leg of the fourth clip and a second end of the body.

2. The system of claim 1, wherein the first notch has a generally U-shaped cross-section and the second notch has a generally U-shaped cross-section.

3. The system of claim 1, wherein the first leg and the second leg are resilient.

4. The system of claim 1, wherein the clip is formed of a plastic material.

5. The system of claim 1, wherein the clip is monolithic.

6. The system of claim 1, further comprising a tube coupled to the substrate via the first clip, the second clip, and the third clip.

7. The system of claim 6, wherein the tube is coupled to the substrate via the first clip such that (i) a first portion of the tube is positioned within a first one of the at least two tube-engaging regions and (ii) a second portion of the tube is positioned within a second one of the at least two tube-engaging regions.

8. The system of claim 6, wherein each of the at least two tube-engaging regions include a plurality of teeth configured to contact the tube.

9. The system of claim 6, wherein the tube is coupled to the substrate via the first clip, the second clip, and the third clip to aid in maintaining the tub in a generally circular, coiled shape.

10. The system of claim 9, wherein the first clip, second clip, and third clip are all angled such that each of the first clip, the second clip, and third clip are at different orientation with respect to one another.

11. The system of claim 1 wherein each of the at least two tube-engaging regions has a generally circular cross-section except for an inlet area opposing the body.

12. The system of claim 1, wherein the substrate includes a plastic material, a metal material, a paper material, polyethylene, high density polyethylene, polypropylene, solid bleached sulphate (SBS) board, paperboard, cardboard, or any combination thereof.

13. The system of claim 1, further comprising a tool clip, the tool clip having:
a tool-clip body,
a pair of curved fingers extending from the tool-clip body generally in the first direction to form a tool-engaging region,
a first leg adjacent to a first end of the tool-clip body that extends from the tool-clip body generally in the second direction,
a second leg adjacent to a second opposing end of the tool-clip body that extends from the body generally in the second direction,
a first tool-clip notch adjacent to the first end of the tool-clip body and configured to receive a third portion of the substrate therein, and
a second tool-clip notch adjacent to the second end of the tool-clip body and configured to receive a fourth portion of the substrate therein.

14. The system of claim 13, wherein the substrate further has a third plurality of apertures positioned generally within a shape formed by the first plurality of apertures.

15. The system of claim 14, wherein the tool-clip is configured to engage an inner edge of a first one of the third plurality of apertures and an inner edge of a second one of the third plurality of apertures simultaneously.

16. The system of claim 14, wherein the tool-clip is configured to engage an outer edge of a first one of the third plurality of apertures and an outer edge of a second one of the third plurality of apertures simultaneously.

17. The system of claim 13, wherein the pair of curved fingers includes a first curved finger defining a first tool-engaging region and a second curved finger defining a second tool-engaging region.

18. The system of claim 17, wherein the first tool-engaging region is defined only by the first curved finger, such that the first curved finger is positioned between the first tool-engaging region and the second curved finger and wherein the second tool-engaging region is defined only by the second curved finger, such that the second curved finger is positioned between the second tool-engaging region and the first curved finger.

19. The system of claim 17, wherein the first curved finger includes a first terminus extending away from the first curved finger and the second curved finger, and wherein the second curved finger includes a second terminus extending away from the second curved finger and the first curved finger, the first terminus and the second terminus being configured to aid a tool in being maintained within the first tool-engaging region and the second tool-engaging region.

20. The system of claim 19, wherein at least a portion of the first tool-engaging region is defined between the first leg and the first terminus of the first curved finger, and wherein at least a portion of the second tool-engaging region is defined between the second leg and the second terminus of the second curved finger.

* * * * *